US 11,351,143 B1

United States Patent
Milner et al.

(10) Patent No.: US 11,351,143 B1
(45) Date of Patent: Jun. 7, 2022

(54) METHODS OF TREATING AMYOTROPHIC LATERAL SCLEROSIS

(71) Applicant: RETROTOPE, INC., Los Altos, CA (US)

(72) Inventors: Peter Milner, Los Altos, CA (US); Mikhail Sergeevich Shchepinov, Kingston Upon Thames (GB)

(73) Assignee: RETROTOPE, INC., Los Altos, CA (US)

( * ) Notice: Subject to any disclaimer, the term of this patent is extended or adjusted under 35 U.S.C. 154(b) by 0 days.

(21) Appl. No.: 17/169,271

(22) Filed: Feb. 5, 2021

(51) Int. Cl.
*A61K 31/232* (2006.01)
*A61P 25/28* (2006.01)
*A61K 31/202* (2006.01)

(52) U.S. Cl.
CPC .......... *A61K 31/232* (2013.01); *A61K 31/202* (2013.01); *A61P 25/28* (2018.01)

(58) Field of Classification Search
None
See application file for complete search history.

(56) References Cited

U.S. PATENT DOCUMENTS

2019/0282529 A1* 9/2019 Shchepinov ......... A61K 31/557

OTHER PUBLICATIONS

Brenna, J. Thomas et al. (2020, e-published Aug. 29, 2020). "Plasma and Red Blood Cell Membrane Accretion and Pharmacokinetics of RT001 (bis-Allylic 11,11-D2-Linoleic Acid Ethyl Ester) during Long Term Dosing in Patients." Journal of Pharmaceutical Sciences, 109(11), 3496-3503. https://doi.org/10.1016/j.xphs.2020.08.019.

Non-Final Office Action issued in U.S. Appl. No. 16/997,692, dated Feb. 4, 2022, 43 pages.

* cited by examiner

*Primary Examiner* — Jeffrey S Lundgren
*Assistant Examiner* — Michael J Schmitt
(74) *Attorney, Agent, or Firm* — Mintz, Levin, Cohn, Ferris, Glovsky and Popeo, P.C.

(57) ABSTRACT

Disclosed are methods for inhibiting the progression of Amyotrophic Lateral Sclerosis (ALS). The methods include administering to a patient suffering from ALS a composition comprising either deuterated linoleic acid or an ester or deuterated arachidonic acid or an ester thereof.

4 Claims, No Drawings

METHODS OF TREATING AMYOTROPHIC LATERAL SCLEROSIS

TECHNICAL FIELD

The invention relates to methods for inhibiting the progression of Amyotrophic Lateral Sclerosis (ALS). The methods include administering to a patient suffering from ALS a composition comprising a deuterated arachidonic acid, a deuterated arachidonic acid ester, or a prodrug of either using a dosing regimen that provides for in vivo concentrations of deuterated arachidonic acid at a level where the progression of the disease is markedly reduced.

BACKGROUND

ALS is a late-onset, progressive neurological disease with its corresponding pathological hallmarks including progressive muscle weakness, atrophy and spasticity which reflects the degeneration and death of upper or lower motor neurons. Once diagnosed, most patients undergo a rapid rate of disease progression terminating in death typically within 3 to 4 years with some patients succumbing even earlier.

The rate of disease progression for a patient with ALS in the absence of therapy as described is referred to as the "natural history" of the disease. The ALSFRS-R is a standard test to determine the rate of loss of muscle functionality over time and is used to measure disease progression. This test has 12 components each of which are measured on a 0 (worse) to 4 (best) scale. The ability of a drug to attenuate the rate of disease progression evidences its efficacy. Recently, a report showed that a two-drug combination administered over a 24-week period provided for an ALSFRS-R 2.4 unit betterment in the rate of disease progression over untreated group. This report further stated that it was equivalent to 6 weeks of less progression of the disease and was considered to be an exciting clinical result. See, e.g., sitn.hms.harvard.edu/flash/2020/slowing-als-with-a-two-drug-therapy/

As to ALS, the most common occurrence is the sporadic ALS (sALS) variant, that is, without any obvious genetic component. However, about ~2% of all cases have a familial ALS (fALS) genetic component. fALS is caused by mutation in Cu/Zn superoxide dismutase (SOD1). There are more than 100 mutation sites in SOD1 that are associated with fALS. Mutation is believed to increase the conformation flexibility of SOD1, giving rise to a misfolded SOD population. Alternatively, without any mutations, the SOD1 protein can become pathogenic via oxidation or aggregation. (Bosco D., et al., Wild-type and mutant SOD1 share an aberrant conformation and a common pathogenic pathway in ALS. *Nat. Neurosci.* 13(11): 1396-1403 (2010)). Therefore, individuals who do not carry a mutant SOD1 could still develop ALS with aggregated or oxidized SOD1.

Oxidative damage of the lipid components of motor neurons is implicated in the pathogenesis of ALS. Such damage is the result of oxidative stress where an imbalance between routine production and detoxification of reactive oxygen species ("ROS") leads to oxidative attack on the lipid membrane of cells. The lipid membrane as well as the endoplasmic reticulum and mitochondria of motor neurons is highly enriched in arachidonic acid (a 20-carbon chain polyunsaturated fatty acid ("PUFA") having 4 sites of cis-unsaturation). Separating each of these 4 sites are 3 bis-allylic methylene groups. These groups are particularly susceptible to oxidative damage due to ROS, and to enzymes such as cyclooxygenases, cytochromes and lipoxygenases, as compared to allylic methylene and methylene groups.

Moreover, once a bis-allylic methylene group in one arachidonic acid is oxidized by a ROS, a cascade of further oxidation of other arachidonic acid groups in the lipid membrane occurs. This is because a single ROS generates oxidation of a first arachidonic acid component through a free radical mechanism which, in turn, can oxidize a neighboring arachidonic acid through the same free radical mechanism which yet again can oxidize another neighboring arachidonic acid in a process referred to as lipid chain auto-oxidation. The resulting damage includes a significant number of oxidized arachidonic acid components in the cell membrane.

Oxidized arachidonic acids negatively affect the fluidity and permeability of cell membranes in motor neurons. In addition, they can lead to oxidation of membrane proteins as well as being converted into a large number of highly reactive carbonyl compounds. The latter include reactive species such as acrolein, malonic dialdehyde, glyoxal, methylglyoxal, etc. (Negre-Salvayre A, et al. Brit. J. Pharmacol. 2008; 153:6-20). But the most prominent products of arachidonic acid oxidation are alpha, beta-unsaturated aldehydes such as 4-hydroxynon-2-enal (4-HNE; formed from n-6 PUFAs like LA or AA), and corresponding ketoaldehydes (Esterfbauer H, et al. Free Rad. Biol. Med. 1991; 11:81-128.

These reactive carbonyls cross-link (bio)molecules through Michael addition or Schiff base formation pathways and have been implicated in a large number of pathological processes such as age-related and oxidative stress-related conditions, and aging.

While it is known that oxidative stress of PUFAs contributes to some extent to the pathogenesis of a number of different diseases including neurological diseases, the underlying etiology of each such disease is so different that it is not possible to predict that a treatment providing positive results for one such oxidative mediated disease is also applicable to another such disease. Still further, given that the vast majority of ALS patients suffer from sALS where the underlying etiology is unknown, the applicability of a given treatment protocol across a spectrum of potentially divergent etiologies for ALS is unpredictable.

Heretofore, the treatment of a variety of neurological diseases including ALS using deuterated 11,11-D2-linoleic acid or an ester thereof, including those in a lipid bilayer form, was disclosed in WO 2011/053870, WO 2012/148934, and WO 2020/102596. Each of these references disclosed the in vivo conversion of 11,11-D2-linoleic acid to 13,13-D2-arachidonic acid which was then incorporated into the motor neurons to stabilize these neurons from oxidative damage. However, these references and other such disclosures failed to suggest a therapeutic level of 13,13-D2-arachidonic acid or other deuterated arachidonic acid compounds in vivo let alone in vivo concentrations of 13,13-D2-arachidonic acid that significantly reduce the rate of progression of ALS.

In view of the above, methods that significantly reduce the rate of progression of ALS in a patient are urgently needed. Such methods would allow for patients to achieve a much longer period of retained muscle functionality and likely a longer lifespan.

SUMMARY

This invention is directed, in part, to the discovery that the progression of ALS in patients is significantly attenuated by a dosing regimen that administers a deuterated arachidonic acid, a deuterated arachidonic acid ester as well as a prodrug of both. One suitable prodrug includes deuterated linoleic acid or esters where, upon ingestion and absorption, hepatic conversion of a portion of the deuterated linoleic acid occurs in vivo to produce deuterated arachidonic acid. As such, deuterated linoleic acid or an ester thereof constitute both an essential fatty acid but also a prodrug of deuterated arachidonic acid. Deuterated arachidonic acid or an ester thereof can be administered directly to the patient thereby bypassing the need for hepatic conversion. In either case, deuterated arachidonic acid is transported to the spinal fluid in the CNS and is taken up by motor neurons.

The inclusion of deuterium into the deuterated arachidonic acid stabilizes the arachidonic acid against oxidative damage which, in turn, minimizes damage to the motor neurons. Still further, it has been found that when concentrations of deuterated arachidonic acid reach a therapeutic level in the motor neurons, the disease progression of ALS is significantly attenuated.

This invention is further directed to the discovery that when the administration involves an effective amount of deuterated linoleic acid or an ester thereof prodrug to a patient with ALS, the dose employed must intrinsically account for the rate that the liver converts the deuterated linoleic acid to the deuterated arachidonic acid.

Likewise, whether the deuterated linoleic acid or the deuterated arachidonic acid (including esters of both) are administered to a patient, proper absorption into the body is controlled by the overall intake of all of the polyunsaturated fatty acids (PUFAs) consumed by the patient. Not all of the daily PUFAs consumed by a patient are absorbed by the body. Rather, the amount absorbed is predicated on several factors including the patient's metabolism and the total amount of PUFAs consumed per day by the patient. Still further, as to linoleic acid, only a fraction of linoleic acid so absorbed is converted to arachidonic acid.

These variable functions in the amount of deuterated linoleic acid or deuterated arachidonic acid consumed and actually absorbed by the body pose a challenge to the dosing regimen. Moreover, it is preferable that the dosing regimen also address the challenge of providing for a dosing regimen that allows for rapid onset to quickly reduce the rate of disease progression in the patient so as to minimize the additional loss of functionality and then to maintain such a reduced rate. It being understood that reducing the rate of disease progression correlates to longer periods of retained functionality in the patient and likely a longer lifespan. Accordingly, the faster one reaches such a reduced rate, the better off it is for the patient.

In one embodiment, this invention addresses this challenge by employing a dosing regimen which delivers deuterated arachidonic acid, deuterated arachidonic acid ester, or a prodrug of both in amounts sufficient to provide for a therapeutic amount of deuterated arachidonic acid in the motor neurons. When so incorporated, the deuterated arachidonic acid reduces the degree of LPO which, in turn, effectively limits progression of ALS provided it is administered in appropriate amounts.

In one embodiment, the reduction in the rate of disease progression is ascertained by methods provided in detail below wherein the delta between the rate of disease progression in the natural history is compared to that found during the therapy described herein. In both cases, the values are first annualized to a common time period and the delta is recorded as an absolute number. In one embodiment, the percent change between the rate of disease progression occurring during the natural history of the patient and the decrease in the rate of disease progression during therapy is at least 30%, preferably at least 40%, more preferably at least 65% and most preferably greater than 70% or 80%. Accordingly, in some embodiments, methods disclosed herein provide for determining a percent reduction in the rate of disease progression by (i) determining a natural rate of disease progression in a patient or an average natural rate of disease progression in a cohort of patients, (ii) determining the rate of disease progression in the patient or cohort of patients during a period of compliance with administration of deuterated arachidonic acid, an ester thereof, or a prodrug thereof, and (iii) measuring the difference between the natural rate and the rate during the period of compliance and dividing the difference by the rate of disease progression during the natural history of the patient. The numerical value is then normalized by multiplying by 100.

Preferably, the concentration of a specific deuterated arachidonic acid found in the motor neuron is sufficient to provide at least a 30% reduction in the rate of disease progression in a patient. As demonstrated in the Examples below, the concentration of deuterated arachidonic acid in red blood cells can be correlated to that found in the spinal fluid from which motor neurons obtain their cellular components. In turn, the motor neurons acquire arachidonic acid from the spinal fluid and, as such, there is a direct corollary between the concentration in the spinal fluid and that in the motor neurons.

Therefore, the concentration of deuterated arachidonic in red blood cells acts as a proxy for the concentration in the motor neurons.

Table 1 below shows the concentration of certain deuterated arachidonic acids that provide for a significant reduction in the rate of disease progression.

TABLE 1

| Deuterated PUFA | Conc. * | Preferred Conc. * | More Preferred Conc. * | Most Preferred Conc. * |
|---|---|---|---|---|
| 13,13-D2-arachidonic acid or ester | at least about 3% | at least about 5% | at least about 8% | at least about 10% |
| 7,7,10,10,13,13-D6-arachidonic acid or ester | at least about 0.5% | at least about 1% | at least about 1.5% or at least about 2% | at least about 2.5% or at least about 3% |

* in red blood cells

As shown in Example 1, the concentration of 13,13-D2-arachidonic acid found in the spinal fluid at 1 month after initiating a dosing regimen of 9 grams per day is about 8% of the total lipids found therein. Since motor neurons obtain their fatty acids from the spinal fluid, the amount of 13,13-D2-arachidonic acid in the spinal fluid corresponds to that in the motor neurons. Moreover, a 3% concentration of 13,13-D2-arachidonic acid in the red blood cells has been shown to correlate to a significant reduction in the rate of disease progression. Accordingly, for the purposes of this application, it is understood that any reference to the concentration of a 13,13-D2-arachidonic acid in the red blood cells that is above 3% correlates to a therapeutic dosing.

In one embodiment, one can measure whether the concentration of a given deuterated arachidonic acid in motor neurons is therapeutic by administering a defined amount of a deuterated arachidonic acid, a deuterated arachidonic acid ester, or a prodrug of both to a subject over a period of at least 1 month; measuring the amount of deuterated arachidonic acid in red blood cells of the subject; measuring whether the concentration of deuterated arachidonic acid in the red blood cells equates to therapeutic amounts as set forth herein; and confirming that the concentration is therapeutic.

In one embodiment, this invention provides for a method for reducing the rate of disease progression of ALS in a patient which method comprises: administering daily an effective amount of a deuterated arachidonic acid, a deuterated arachidonic acid ester, or a prodrug thereof, to reduce the rate of disease progression; wherein the concentration of deuterated arachidonic acid in the motor neurons is sufficient to reduce the rate of disease progression by at least about 30% as compared to the rate of disease progression during the natural history of the patient.

In one embodiment, the percentage of reduction in the rate of disease progression is ascertained by measuring the natural rate of disease progression in a patient or an average rate in a cohort of patients and measuring the rate of disease progression in said patient or cohort of patients during compliance with this method, measuring the delta (i.e., difference) between the two in absolute numbers, dividing the delta by the natural history, and then multiplying by 100.

In one embodiment, when a prodrug of a deuterated arachidonic acid or ester thereof is employed, it is a deuterated linoleic acid or an ester thereof.

In one embodiment, the deuterated linoleic acid or ester thereof is 11,11-D2-linoleic acid or ester thereof.

In one embodiment, the deuterated arachidonic acid or ester thereof is 13,13-D2-arachidonic acid.

In one embodiment, a therapeutic concentration of 13,13-D2-arachidonic acid in red blood cells is at least about 3% based on the total number of fatty acids contained in the red blood cells.

In one embodiment, the deuterated arachidonic acid or ester thereof is 7,7,10,10-D4-arachidonic acid or ester thereof; or 10,10,13,13-D4-arachidonic acid or ester thereof; or 7,7,13,13-D4-arachidonic acid.

In one embodiment, a therapeutic concentration of D4-arachidonic acids in the red blood cells is at least about 1% based on the total number of fatty acids contained therein.

In one embodiment, when a deuterated linoleic acid or ester thereof is used (e.g., 11,11-D2-linoleic acid or ester thereof), the deuterated linoleic acid is bio-converted in vivo to a deuterated arachidonic acid (e.g., 13,13-D2-arachidonic acid). For example, sufficient amounts of 11,11-D2-linoleic acid or ester thereof are administered to the patient such that the concentration 13,13-D2-arachidonic acid in the red blood cells is at least about 3% and preferably at least about 5% based on the total number of fatty acids contained in the red blood cells. Alternatively, one can bypass the required hepatic conversion by directly administering 13,13-D2-arachidonic acid to the patient at a sufficient amount so as to provide about 3% and preferably at least about 5% of this acid in the red blood cells.

In one embodiment, the deuterated arachidonic acid or ester thereof is 7,7,10,10,13,13-D6-arachidonic acid or ester thereof. Sufficient amounts of 7,7,10,10,13,13-D6-arachidonic acid or ester thereof are administered to the patient such that it's concentration in the red blood cells is at least about 0.5% based on the total number of fatty acids contained therein.

In one embodiment, this invention provides for a tiered dosing regimen comprising two components. The first component takes into account the factors set forth above and delivers a primer or an accelerated dosing of deuterated arachidonic acid (including esters thereof) or a prodrug thereof. This primer dose provides sufficient amounts of deuterated linoleic acid or an ester thereof or a deuterated arachidonic acid or an ester thereof that are to be absorbed by the patient. In the case of deuterated linoleic acid or an ester thereof, sufficient amounts are administered to account for that portion which is bio-converted to deuterated arachidonic acid. Regardless, the amount of deuterated arachidonic acid incorporated into the motor neurons is sufficient to result in a significant reduction in the rate of disease progression.

This invention is predicated on the discovery that when the concentration of deuterated arachidonic acid in the motor neurons is allowed to increase to a therapeutic level, the progression of the disease is significantly attenuated. The primer dose is continued for a period of up to about 45 days to ensure that the concentration of deuterated arachidonic acid reaches therapeutic levels.

Still further, when administered, deuterated linoleic acid requires hepatic conversion of a portion of that PUFA to provide for deuterated arachidonic acid. This invention is also predicated on the discovery that this conversion lags behind the time of administration of deuterated linoleic acid by several days. Indeed, a patient transitioning from the primer dose component to the maintenance dose continued to generate increased amounts of deuterated arachidonic acid well after initiation of the maintenance dose that utilized less deuterated linoleic acid or an ester thereof.

Based on this discovery, one can avoid the need to have hepatic conversion of deuterated linoleic acid to deuterated arachidonic acid by administering the deuterated arachidonic acid directly. This, in turn, will lead to a more rapid delivery of a therapeutic level of deuterated arachidonic acid into the motor neurons and an earlier reduction in the rate of progression of the disease.

Still further, the fact that two of the three bis-allylic sites on the arachidonic acid are deuterated in the D4-arachidonic acids described above advantageously increases the stability of the fatty acids in the motor neurons against lipid chain auto-oxidation. It is contemplated that this enhanced stability will allow for less D4-arachidonic acid to be present in the motor neurons while still providing excellent attenuation in the rate of disease progression. As such, the primer dose of D4-arachidonic acid can use from about 1 to about 6 grams per day and any subrange or number therebetween. Such reduced amounts are designed to provide for concentrations of D4-arachidonic acid in the fatty acids of the phospholipids as shown above in Table 1. In a preferred embodiment, the primer dose comprises about 1 to about 5 grams of D4-arachidonic acid or any subrange or number therebetween.

Still further, the fact that all three bis-allylic sites on the arachidonic acid are deuterated in 7,7,10,10,13,13-D6-arachidonic acid advantageously maximizes the stability of the fatty acids in the motor neurons against lipid chain auto-oxidation. It is contemplated that this enhanced stability will allow for less 7,7,10,10,13,13-D6-arachidonic acid to be present in the motor neurons while still providing excellent attenuation in the rate of disease progression. As such, the primer dose of 7,7,10,10,13,13-D6-arachidonic acid can use from about 0.5 to about 5 grams per day and any subrange or number therebetween. Such reduced amounts are designed to provide for concentrations of 7,7,10,10,13,13-D6-arachidonic acid in the fatty acids of the phospholipids as shown above in Table 1. In a preferred embodiment, the primer dose comprises about 0.5 to about 4 grams of 7,7,10,10,13,13-D6-arachidonic acid or any subrange or number therebetween for said dosing.

In one preferred embodiment, when dosing 11,11-D2-linoleic acid or an ester thereof, the primer dose in the methods of this invention is sufficient to provide for a concentration of at least about 3 percent and preferably about 5 percent of 13,13-D2-arachidonic acid in the red blood cells within no more than about 45 days from initiation of treatment and preferably by about 30 days. The maintenance dose then maintains that percentage of 13,13-D2-arachidonic acid in motor neurons although with some tolerance such that the lower limit of no less than about 2.7 percent or so in the red blood cells.

In one embodiment, the primer dose of the 11,11-D2-linoleic acid or an ester thereof is preferably from about 7 to about 12 grams and is continued for at least about 24 days. The upper end for daily or periodic administration is determined by the attending clinician based on the degree of disease progression in the patient coupled with the patient's age, weight and other conditions and can run for up to about 60 days or longer. In one preferred embodiment, the primer dose is continued from a period of from about 24 days up to about 45 days or any number of days or ranges therebetween.

This primer dose is used so as to provide rapid onset to the targeted concentrations of 13,13-D2-arachidonic acid in the red blood cells and, by correlation, in the motor neurons. This primer dose is designed to compensate for variability in the patient's rate of metabolic conversion of 11,11-D2-linoleic acid to 13,13-D2-arachidonic acid. Preferred daily or periodic dosing of 11,11-D2-linoleic acid or ester thereof in the primer dose ranges from about 7 to about 12 grams per day and includes about 7 gm, about 7.5 gm, about 8 gm, about 8.5 gm, about 9 gm, about 9.5 gm, about 10 gm, about 10.5 gm, about 11 gm, about 11.5 gm, and about 12 gm.

As shown in Example 2, a primer dose of 9 grams of 11,11-D2-linoleic acid over a period of 30 days followed by a maintenance dose of 5 grams of 11,11-D2-linoleic acid provide for substantial reduction in the rate of disease progression.

The maintenance dose is initiated after completion of the primer dose and involves a reduced daily or periodic dose of deuterated linoleic acid or ester thereof or the deuterated arachidonic acid or ester thereof. This reduced amount is described as a maintenance amount that provides for sufficient deuterated arachidonic acid in vivo to maintain a sufficient concentration of deuterated arachidonic acid in the spinal fluid and, hence, in the motor neurons. In general, the maintenance dose comprises about 30 to about 70 percent of the amount of deuterated linoleic acid or an ester thereof used in the primer dose. In one embodiment, the maintenance dose comprises about 35 to about 65 percent of the amount of deuterated linoleic acid or deuterated arachidonic acid (including esters of both). In either case, the maintenance dose is less than the dosing dose.

In one embodiment, at the termination of the primer dose, the amount of 11,11-D2-linoleic acid or an ester thereof administered to the patient in the maintenance dose ranges from about 3 to about 6.5 gm per day. This reduced dosing of 11,11-D2-linoleic acid during the maintenance dose provides for maintenance of the targeted concentrations of 13,13-D2-arachidonic acid in the motor neurons of the patient. Preferred daily or periodic dosing of 11,11-D2-linoleic acid or ester thereof in the maintenance dose includes about 3 gm, about 3.5 gm, about 4 gm, about 4.5 gm, about 5 gm, about 5.5 gm, about 6 gm, and about 6.5 gm of 11,11-D2-linoleic acid or ester thereof.

In one embodiment, when dosing 7,7,10,10,13,13-D6 arachidonic acid or an ester thereof, the primer dose in the methods of this invention allows for the concentration of 7,7,10,10,13,13-D6 arachidonic acid in the motor neurons to reach at least about 0.5 percent or about 1.0 percent or about 1.5 percent or about 2 percent or about 2.5 percent of the total phospholipid components the motor neurons within no more than about 45 days from initiation of treatment and preferably by about 30 days. The maintenance dose maintains that percent concentration of 7,7,10,10,13,13-D6 arachidonic acid in motor neurons and preferably at least at about 90% of the concentration established during the primer dose.

In one embodiment, the primer dose employs from about 0.5 to about 5 grams and any number or subrange therebetween and is continued for at least about 24 days. The upper end for daily or periodic administration is determined by the attending clinician based on the degree of disease progression in the patient coupled with the patient's age, weight and other conditions and can run for up to about 60 days or longer. In one preferred embodiment, the primer dose is continued from a period of from about 24 days up to about 45 days or any number of days therebetween.

The maintenance dose is initiated after completion of the primer dose and involves a reduced daily or periodic dose of 7,7,10,10,13,13-D6 arachidonic acid or an ester thereof. This reduced amount is that amount that provides for sufficient deuterated arachidonic acid in vivo to maintain a therapeutic concentration of 7,7,10,10,13,13-D6 arachidonic acid in the motor neurons. In general, the maintenance dose comprises about 30 to about 70 percent of the amount of 7,7,10,10,13,13-D6 arachidonic acid or an ester thereof used in the primer dose. In one embodiment, the maintenance dose comprises about 35 to about 65 percent of the amount of 7,7,10,10,13,13-D6 arachidonic acid or an ester thereof.

In one embodiment, the patients are placed on a diet that restricts intake of excessive amounts of linoleic acid, arachidonic acid, and/or other PUFA compounds so as to avoid insufficient uptake of the deuterated linoleic acid or the deuterated arachidonic acid by the body. Generally, dietary components that contribute to excessive amounts of PUFA consumed are restricted. Such dietary components include, for example, fish oil pills, products that contain high levels of PUFAs such as salmon, and patients on conventional feeding tubes that result in excessive PUFA intake. In a preferred embodiment, the methods described herein include both the dosing regimen described above as well as placing the patients on a restrictive diet that avoids excessive ingestion of PUFA components.

In one embodiment, this invention provides for a method for reducing the rate of disease progression in a patient suffering from ALS which method comprises administering 11,11-D2-linoleic acid or an ester thereof to the patient with a dosing regimen that comprises a primer dosing and a maintenance dosing schedule which comprise:

a) said first dosing component comprises administering to said patient primer dose of 11,11-D2-linoleic acid or an ester thereof in an amount to sufficient and for a period of time to allow for reduction in the rate of disease progression within no more than about 45 days from start of dosing;

b) subsequently following said primer dose, initiating a maintenance dosing to said patient said dosing comprises an amount of 11,11-D2-linoleic acid or an ester thereof in an amount sufficient to maintain the concentration of 13,13-D2-arachidonic acid in the motor neurons wherein the amount of 11,11-D2-linoleic acid or ester thereof administered in said maintenance dose is less than the amount administered in said primer dose; and optionally:

c) monitoring the concentration of 13,13-D2-arachidonic acid in the patient to ensure that the patient is maintaining a therapeutic concentration of 13,13-D2-arachidonic acid; and d) increasing the dosing of 11,11-D2-linoleic acid or an ester thereof when said concentration of 13,13-D2-arachidonic acid is deemed to be less than a therapeutic amount.

In one embodiment, the therapeutic amount of 13,13-D2-arachidonic acid in the motor neurons is determined by extrapolation from its concentration in red blood cells as provided herein. Generally, a concentration of 13,13-D2-arachidonic acid of about 3 percent in red blood cells based on the total weight of fatty acids therein is deemed to be therapeutic. However, when evaluating whether there should be an increase in the amount of 11,11-D2-linoleic acid or an ester thereof administered to the patient in the second component of the dosing schedule, the attending clinician can determine that a red blood concentration as low as about 2.7 percent is still therapeutic.

In one embodiment, this invention provides for a method for reducing the rate of disease progression in a patient suffering from ALS which method comprises administering 11,11-D2-linoleic acid or an ester thereof to the patient with a dosing regimen that comprises a primer dosing and a maintenance dosing schedule which comprise:

a) said primer dose comprises administering daily or periodically to said patient at least about 7 grams of 11,11-D2-linoleic acid or an ester thereof wherein said first daily or periodic dosing component is continued for a period of from about 24 to about 45 days to provide a therapeutic concentration of 13,13-D2-arachidonic acid in the motor neurons thereby reducing the rate of disease progression;

b) subsequently following said primer dose with a maintenance dose which comprises daily or periodic administration to said patient of about at least 3 grams of 11,11-D2-linoleic acid or an ester thereof to maintain a therapeutic concentration of 13,13-D2-arachidonic acid provided that said maintenance dose is less than said primer dose; and optionally:

c) monitoring the concentration of 13,13-D2-arachidonic acid in the patient to ensure that the patient maintains a therapeutic concentration of 13,13-D2-arachidonic acid; and d) increasing the dosing of 11,11-D2-linoleic acid or an ester thereof when said concentrations of 13,13-D2-arachidonic acid is deemed to be less than a therapeutic concentration.

In one embodiment, this invention provides for a method for reducing the rate of disease progression in a patient suffering from ALS which method comprises administering 11,11-D2-linoleic acid or an ester thereof to the patient with a dosing regimen that comprises a primer dosing and a maintenance dosing schedule which comprise:

a) said first primer dose comprises about 9 grams of 11,11-D2-linoleic acid or an ester thereof wherein said daily or periodic primer dose is continued for about 30 days to 45 days, and preferably about 30 days, to provide a therapeutic concentration of 13,13-D2-arachidonic acid in the motor neurons thereby reducing the rate of disease progression;

b) subsequently following said daily or periodic primer dose with a daily or periodic maintenance dose of about 5 grams of 11,11-D2-linoleic acid or an ester thereof to maintain a therapeutic concentration of 13,13-D2-arachidonic acid in the motor neurons; and optionally c) monitoring the concentration of 13,13-D2-arachidonic acid in the patient to ensure that the patient maintains a therapeutic concentration of 13,13-D2-arachidonic acid; and d) increasing the dosing of 13,13-D2-arachidonic acid or an ester as well as a prodrug thereof when said concentrations of 13,13-D2-arachidonic acid is deemed to be less than a therapeutic concentration of 13,13-D2-arachidonic acid.

In one embodiment, a therapeutic amount of 13,13-D2-arachidonic acid in red blood cells is at least about 3% of the total fatty acids in these cells whether delivered by 11,11-D2-linoleic acid which is converted to 13,13-D2-arachidonic acid or by direct administration of 13,13-D2-arachidonic acid or by a mixture of 11,11-D2-linoleic acid or 13,13-D2-arachidonic acid or by administering 13,13-D2-arachidonic acid in either the first or second component of the dosing regimen In another embodiment, the therapeutic concentration of 13,13-D2-arachidonic acid in the motor neurons correlates to a concentration of 13,13-D2-arachidonic acid of at least about 5% of the total fatty acids in red blood cells independent of whether the 13,13-D2-arachidonic acid concentration is achieved by administering 11,11-D2-linoleic acid or an ester thereof or by administering 13,13-D2-arachidonic acid or an ester thereof as well as by a mixture thereof.

In one embodiment, this invention provides for a method for reducing the rate of disease progression in a patient suffering from ALS which method comprises administering 7,7,10,10,13,13-D6 arachidonic acid or an ester thereof to the patient with a dosing regimen that comprises a primer dose and a maintenance dose comprising:

a) a primer dose comprising administering daily or periodically to said patient an amount of 7,7,10,10,13,13-D6 arachidonic acid or an ester thereof in an amount to sufficient and for a period of time to reduce the rate of disease progression within no more than about 45 days from start of dosing; and b) subsequently following said primer dose with administering daily or periodically to said patient a maintenance dose which comprises a sufficient amount of 7,7,10,10,13,13-D6 arachidonic acid or an ester thereof to maintain a therapeutic concentration of 7,7,10,10,13,13-D6 arachidonic acid in the motor neurons wherein the amount of 7,7,10,10,13,13-D6 arachidonic acid or ester thereof administered in said second dose component is less than the amount administered in said first dose component; and optionally c) monitoring the concentration of 7,7,10,10,13,13-D6 arachidonic acid in the cellular membrane of the patient to ensure that the patient maintains a therapeutic concentration of 7,7,10,10,13,13-D6 arachidonic acid; and d) increasing the dosing of 7,7,10,10,13,13-D6 arachidonic acid or an ester thereof when said concentrations of 7,7,10,10,13,13-D6 arachidonic is deemed to be less than a therapeutic concentration.

In another embodiment, this invention provides for a method for reducing the rate of disease progression in a patient suffering from ALS which method comprises administering 7,7,10,10,13,13-D6 arachidonic acid or an ester thereof to the patient with a dosing regimen that comprises a primer dose and a maintenance dose comprising:

a) a daily or periodic primer dose comprising administering daily or periodically to said patient at least about 0.5 grams of 7,7,10,10,13,13-D6 arachidonic acid or an ester thereof wherein said primer dose is continued a period of from about 24 to about 45 days; and b) subsequently following said daily or periodic primer dose with said daily or periodic maintenance dose which is from about 30 to 65% of the amount of 7,7,10,10,13,13-D6 arachidonic acid or ester thereof administered in said primer dose; and optionally c) monitoring the concentration of 7,7,10,10,13,13-D6 arachidonic acid in the patient to ensure that the patient maintains a therapeutic concentration of said 7,7,10,10,13,13-D6 arachidonic acid; and d) increasing the dosing of 7,7,10,10,13,13-D6 arachidonic acid or an ester thereof when said concentrations of 7,7,10,10,13,13-D6-arachidonic acid is deemed to be less than a therapeutic concentration of 7,7,10,10,13,13-D6-arachidonic acid.

In one embodiment, each of the first and second daily or periodic dosing components are administered in a single setting in two settings or in three settings.

In one embodiment, the concentration of 13,13-D2-arachidonic acid or 7,7,10,10,13,13-D6-arachidonic acid can be measured by measuring the concentration of 11,11-D2-linoleic acid, 13,13-D2-arachidonic acid or 7,7,10,10,13,13-D6-arachidonic acid in red blood cells as a percentage of the total amount of fatty acids found therein about 25, 30, 35, 40, 45, 60, or 90 days post initiation of the maintenance dosing. In another embodiment, the concentration of 13,13-D2-arachidonic acid or 7,7,10,10,13,13-D6-arachidonic acid is measured about 30 days post initiation of the maintenance dosing.

In one embodiment, there is provided a kit of parts comprising a multiplicity of containers wherein each container contains a single daily or periodic dose of the first dosing component (e.g., 9 grams) or a single daily or periodic dose of the second dosing component (e.g., 5 grams). In one embodiment, each container comprises a plurality of dosing subunits. In one embodiment, each subunit comprises a pharmaceutical acceptable carrier and about 1 gm of 11,11-D2-linoleic acid such that the aggregate amount of 11,11-D2-linoleic acid in all of the subunits of a single container corresponds to either the first dosing component or the second dosing component.

In one embodiment, the aggregate of the subunits total 9 grams or 5 grams of 11,11-D2-linoleic acid.

In one embodiment, each container provides specific instructions to the patient as to his or her daily or periodic dosing including instructions to ingest all of the prescribed amount of drug.

In one embodiment, this invention provides for a unit dose of 11,11-D2-linoleic acid or an ester thereof comprising either about 9 grams or about 5 grams of 11,11-D2-linoleic acid or as ester thereof.

DETAILED DESCRIPTION OF THE INVENTION

This invention is directed to methods for treating ALS to significantly slow the rate of disease progression in a patient. In one embodiment, the methods of this invention include a dosing regimen that is sufficient to provide a therapeutic level of deuterated arachidonic acid in the motor neurons. In another embodiment, the methods described herein comprise a daily or periodic primer dose that accelerates delivery of deuterated linoleic acid or deuterated arachidonic acid to the patient. This primer dose is continued for a sufficient period of time to achieve a therapeutic concentration of a deuterated arachidonic acid in vivo. At that point, a daily or periodic maintenance dose is employed to maintain the therapeutic concentration of the deuterated arachidonic acid. Preferably, this invention provides for dietary limitations on the daily or periodic amount of naturally occurring PUFAs that is to be consumed in order to avoid limiting absorption of the deuterated linoleic acid or ester thereof which could result in subtherapeutic concentrations of deuterated arachidonic acid in vivo.

Prior to discussing this invention in more detail, the following terms will first be defined. Terms that are not defined are given their definition in context or are given their medically acceptable definition.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +1-10%.

As used herein, the term "comprising" or "comprises" is intended to mean that the compositions and methods include the recited elements, but not excluding others.

As used herein, the term "consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention.

As used herein, the term "consisting of" shall mean excluding more than trace elements of other ingredients and substantial method steps. Embodiments defined by each of these transition terms are within the scope of this invention.

As used herein, the term "ALS" refers to all forms of ALS including sALS and fALS.

As used herein, the term "linoleic acid" refers to the compound and a pharmaceutically acceptable salt thereof having the formula provided below and having the natural abundance of deuterium at each hydrogen atom:

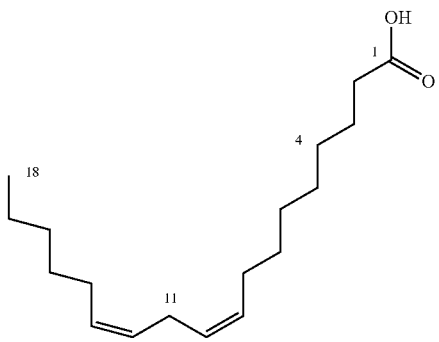 [SMILES: CCCCC/C=C\C/C=C\CCCCCCCC(=O)O]

Esters of linoleic acid are formed by replacing the —OH group with —OR. Such esters are as defined herein below.

As used herein and unless the context dictates otherwise, the term "deuterated linoleic acid or an ester thereof" refers to linoleic acid or ester compounds comprising one or two deuterium atoms at the 11 position thereof and optionally additional deuterium atoms at other positions within the molecule including at position 8. Specific compounds encompassed by this definition include by way of example only 11-D1-linoleic acid, 11,11-D2-linoleic acid, 8,11-D2-linoleic acid, 8,11,11-D3-linoleic acid and 8,8,11,11-D4-linoleic acid as well as esters of any one of these compounds. Additional stabilization of the bis-allylic position could also include replacement of one or more of bis-allylic carbon atoms with a heavy isotope, alone or in conjunction with the deuteration (or tritiation), as the isotope effect (IE) resulting in stabilization of a bond with heavy isotopes is additive per long-established and fundamental chemical principles. (Westheimer, *Chem. Rev.* (1961), 61:265-273; Shchepinov, *Rejuvenation Res.*, (2007), 10:47-59; Hill et al., *Free Radic. Biol. Med.*, (2012), 53:893-906; Andreyev et al., *Free Radic. Biol. Med.*, (2015), 82:63-72. Bigeleisen, J. The validity of the use of tracers to follow chemical reactions. *Science*, (1949), 110:14-16.

As used herein, arachidonic acid has the numbering system as described below:

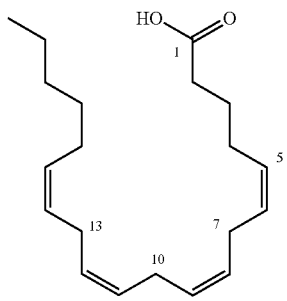 [SMILES: CCCCC/C=C\C/C=C\C/C=C\C/C=C\CCCC(=O)O]

where each of positions 7, 10 and 13 are bis-allylic positions within the structure.

As used herein and unless the context dictates otherwise, the term "deuterated arachidonic acid or an ester thereof" refers to arachidonic acid or ester compounds having at least one deuterium atom at a bis-allylic position and optionally additional deuterium atoms at other positions within the molecule. Specific compounds encompassed by this definition include, by way of example only, 7,7-D2-arachidonic acid, 10,10-D2-arachidonic acid, acid, 13,13-D2-arachidonic acid, 7,7,10,10-D4-arachidonic acid, 7,7,13,13-D4-arachidonic acid, 10,10,13,13-D4-arachidonic acid, 7,7,10,10,13,13-D6-arachidonic acid and perdeurerated arachidonic acid.

As used herein, the term "ester" means any pharmaceutically acceptable ester of a deuterated linoleic acid or a deuterated arachidonic acid such as but not limited to $C_1$-$C_6$ alkyl esters, glycerol (including monoglycerides, diglycerides and triglycerides), sucrose esters, phosphate esters, and the like. The particular ester employed is not critical provided that the ester is pharmaceutically acceptable (non-toxic and biocompatible).

As used herein, the term "phospholipid" refers to any and all phospholipids that are components of the cell membrane. Included within this term are phosphatidylcholine, phosphatidylethanolamine, phosphatidylserine, and sphingomyelin. In the motor neurons, the cell membrane is enriched in phospholipids comprising arachidonic acid.

As used herein, the term "pathology of a disease" refers to the cause, development, structural/functional changes, and natural history associated with that disease. The term "natural history" means the progression of the disease in the absence of treatment.

As used herein, the term "reduced rate of disease progression" means that the rate of disease progression is attenuated after initiation of treatment as compared to the patient's natural history. In one embodiment, the reduced rate of disease progression is measured by using the ALSFRS-R score to determine the rate of disease progression during the natural history and, again, measuring the ALSFRS-R score during the interval starting with therapy and ending at a set period of time thereafter (e.g., 6 months). Both rates are then annualized and a reduced rate of disease progression results in a percentage change of at least 30% between the ALSFRS-R scores before and after.

A "therapeutic concentration" means a concentration of a deuterated arachidonic acid that reduces the rate of disease progression by at least 30%. Since obtaining the concentration of a deuterated arachidonic acid in the motor neurons or in the spinal fluid of a patient is either not feasible or optimal, the therapeutic concentration is based on the concentration of either deuterated linoleic acid or deuterated arachidonic acid found in red blood cells as provided in the Examples below. Accordingly, any reference made herein to a therapeutic concentration of deuterated arachidonic acid is made by evaluating its concentration in red blood cells.

Alternatively, the reduction in the rate of disease progression is confirmed by a reduction in the downward slope (flattening the curve) of a patient's relative muscle functionality during therapy as compared to the downward slope found in the natural history. Typically, the differential between the downward slope measured prior to treatment and the slope measured after at least 90 days from initiation of treatment has a flattening level of at least about 30%. So, a change of 7.5 degrees (e.g., a downward slope of 25 degrees during the natural history that is reduced to a downward slope of 17.5 degrees provides for a 40% decrease in the slope). In any case, the reduction in downward slope evidences that the patient has a reduced rate of disease progression due to the therapy.

As used herein, the term "patient" refers to a human patient or a cohort of human patients suffering from ALS with an average of their disease progression being used.

As used herein, the term "loading or primer amount" refers to an amount of a deuterated linoleic acid or an ester thereof or a deuterated arachidonic acid or an ester thereof that is sufficient to provide for a reduced rate of disease progression within at least about 45 days after initiation of administration and preferably within 30 days. The amount so employed is loaded such that the patient has a stabilized rate of disease progression within this time period. When less than a loading amount is used, it is understood that such can provide therapeutic results but will not achieve the same level of reduction in disease progression. Given the progressive nature of ALS, those dosing regimens that achieve the best reduction in the rate of disease progression are preferred as they are associated with the patient having less loss of muscle functionality over a given period of time.

This invention includes the discovery that the primer doses of 11,11-D2-linoleic acid employed to date are well tolerated by patients and provide for rapid onset of a sufficient amount of deuterated arachidonic acid to provide for a reduced and stabilized rate of disease progression.

As used herein, the term "maintenance dose" refers to a dose of deuterated linoleic acid or an ester thereof or deuterated arachidonic acid that is less than the primer dose and is sufficient to maintain a therapeutic concentration of deuterated arachidonic acid in the cell membrane of red blood cells and, hence, in the cell membrane of motor neurons, that retains a stable rate of disease progression.

As used herein, the term "periodic dosing" refers to a dosing schedule that substantially comports to the dosing described herein. Stated differently, periodic dosing includes a patient who is compliant at least 75 percent of the time over a 30-day period and preferably at least 80% compliant contains a designed pause in dosing. For example, a dosing schedule that provides dosing 6 days a week is one form of periodic dosing. Another example is allowing the patient to pause administration for from about 3 or 7 or days due to personal reasons provided that the patient is otherwise at least 75 percent compliant.

The term "cohort" refers to a group of at least 2 patients whose results are to be averaged.

As used herein, the term "pharmaceutically acceptable salts" of compounds disclosed herein are within the scope of the present invention include acid or base addition salts which retain the desired pharmacological activity and is not biologically undesirable (e.g., the salt is not unduly toxic, allergenic, or irritating, and is bioavailable). When the compound of the present invention has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present invention has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$)ammonia or organic amines (e.g., dicyclohexylamine, trimethylamine, trimethylamine, pyridine, picoline, ethanolamine, diethanolamine, triethanolamine) or basic amino acids (e.g., arginine, lysine, and ornithine). Such salts can be prepared in situ during isolation and purification of the compounds or by separately reacting the purified compound in its free base or free acid form with a suitable acid or base, respectively, and isolating the salt thus formed.

Compound Preparation

11-D1-linoleic acid, 11,11-D2-linoleic acid, 8,8,11,11-D4 linoleic acid (which yields 10,10,13,13-D4-arachidonic acid upon enzymatic desaturation-extension) and other deuterated linoleic acid compounds are known in the art. For example, a variety of deuterated linoleic acids, including 11,11-D2-linoleic acid and esters thereof, are described, for example, in U.S. Pat. No. 10,052,299 which is incorporated herein by reference in its entirety.

11-D1-linoleic acid is commercially available from Cayman Chemical Company, Ann Arbor, Mich., USA 48108.

Likewise, 7,7-D2-arachidonic acid, 10,10-D2-arachidonic acid, 13,13-D2-arachidonic acid, 7,7,10,10-D4-arachidonic acid, 7,7,13,13-D4 arachidonic acid, 10,10,13,13-D4-arachidonic acid, 7,7,10,10,13,13-D6-arachidonic acid are disclosed by Shchepinov, et al., Molecules, 28(12): 3331 et seq. (2018). Other deuterated arachidonic acid compounds are known in the art.

Esters of these deuterated fatty acids are prepared by conventional techniques well known in the art.
Methodology—Deuterated Linoleic Acid Some of the methods of this invention utilize the hepatic conversion of linoleic acid to arachidonic acid by administering deuterated linoleic acid or an ester thereof to a patient in order to biosynthesize a therapeutic concentration of deuterated arachidonic acid for use in the methods described herein.

In one embodiment, 11,11-D2-linoleic acid or ester thereof is administered to the patient in sufficient amounts to generate a concentration of 13,13-D2-arachidonic acid in red blood cells of at least about 3% based on the total number of fatty acids found therein.

In one embodiment, such administration comprises the use of a dosing regimen that includes two dosing components. The first dosing component comprises a primer dose of 11,11-D2-linoleic acid or an ester thereof. The second dosing component comprises a maintenance dose of 11,11-D2-linoleic acid or an ester thereof wherein the amount of 11,11-D2-linoleic acid or an ester thereof in said second dosing component is less than that of the first dosing component.

As to the primer dose, the amount of 11,11-D2-linoleic acid or an ester thereof employed is preferably designed to provide rapid onset of therapy. Such therapy is measured by a reduction in the disease progression of ALS as described below. The primer dose takes into account the various complicating factors such as the amount of PUFAs consumed by the patient in a given day, the in vivo rate of conversion of 11,11-D2-linoleic acid to 13,13-D2-arachidonic acid, as well as the general turnover rate of lipids in the motor neurons.

Regarding this last point, the lipid components of a motor neurons are not static but, rather, are exchanged over time. In general, only a fraction of the lipids in the lipids are replaced each day. In the case of motor neurons, these cells are rich in lipids comprising arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid by the liver.

As to the later, the rate of arachidonic acid synthesized by the liver is typically rate limited to the extent that there is a maximum amount of arachidonic acid that the liver can generate in a given day. In turn, only a fraction of the linoleic acid consumed is converted to arachidonic acid with the majority of the linoleic acid remaining unchanged. This limited rate of hepatic synthesis of arachidonic acid from linoleic acid results in a delay in such synthesis after administration of the deuterated linoleic acid as the amount of 13,13-D2-arachidonic acid concentration in red blood cells continues to increase after converting from the primer dose to the maintenance dose of the dosing regimen. This increase is contra-suggested as the maintenance dosing employs less 11,11-D2-linoleic acid as compared to the primer dose. However, without being limited to any theory, we believe that this increase is due to a lag in the hepatic conversion of 11,11-D2-linoleic acid to 13,13-D2-arachidonic acid after the administration of 11,11-D2-linoleic acid.

Hence, the choice of a dosing of 11,11-D2-linoleic acid must address each of the above components and set a dosing level that allows for the accumulation of a sufficient amount of 11,11-D2-linoleic acid in the body and, hence, the generation of therapeutic levels of 13,13-D2-arachidonic acid in the red blood cells. When so achieved, the data in the Examples establish that there is a significant reduction in the rate of disease progression.

Given the above, the dosing regimen described herein must include sufficient amounts of 11,11-D2-linoleic acid that are absorbed into the patient so as to maximize the in vivo conversion of 11,11-D2-linoleic acid 13,13-D2-arachidonic acid. Once maximized, the resulting the deuterated arachidonic acid accumulates in the body until its concentration is stabilized in the lipid pool of the patient. Stabilization is reached, once the amount of deuterated 13,13-D2-arachidonic acid removed from the body is replaced by an equivalent amount of newly formed 13,13-D2-arachidonic acid. During this process, 13,13-D2-arachidonic acid is systemically absorbed into the cells of the body including motor neurons wherein the rate of which such absorption occurs is based on the exchange rate or turnover rate of lipids in the cell membrane of these motor neurons.

This invention is based on the discovery that given the above variables, the amount of 11,11-D2-linoleic acid or ester thereof that is administered over time and converted in vivo to 13,13-D2-arachidonic acid is selected so that the fatty acids contained red blood cells comprise at least about 3% and preferably at least about 5% of 13,13-D2-arachidonic acid. At that level, the deuterated arachidonic acid concentration stabilizes the cell membrane and limits or prevents the cascade of lipid auto-oxidation. When so administered, there is a significant reduction in the progression rate of ALS.

Other deuterated linoleic acid compounds will typically correspond to the above dosing regimen understanding that the degree of protection may increase or decrease depending on the extent of deuteration.

This invention is also based, in part, on the discovery that when the lipid membrane of motor neurons is stabilized against LPO, there is a substantial reduction in the progression of ALS. This is due to the fact that replacement of hydrogen atoms with deuterium atoms at the bis-allylic positions of arachidonic acid renders the deuterated arachidonic acid significantly more stable to ROS than the hydrogen atoms. As above, this stability manifests itself in reducing the cascade of lipid auto-oxidation.

As to the reduction in the progression of ALS, this can be readily calculated by using the known and established rate functional decline measured by the R—ALS Functional Rating Scale—revised after commencement of drug therapy as compared to the rate of decline prior to drug therapy (natural history of decline). As the rate of decline is not perceptible on a day to day basis, the functional decline is typically measured monthly and is evaluated over a period of time such as every 3 months, every 6 months or annually.

As set forth in the examples below, the rate of functional decline is predicated on measuring an individual's but preferably a cohort average for the natural history of disease progression. Next, the individual or cohort average for the functional decline is then determined at a period of time such as at 3, 6 or 12 months after initiation of therapy. The rate of decline based on the average of the natural history of the cohort is set as the denominator. The numerator is set as the delta between the rate of the natural history of disease progression and the rate of functional decline after a set period of treatment per this invention. The resulting fraction is the multiplied by 100 to give a percent change. The following exemplifies this analysis.

Cohort A has an average natural history rate of decline of 28 annualized for a one (1) year period. Six (6) months after initiation of treatment per this invention, Cohort A records an annualized average rate of decline of 14. This provides a delta of 14 degrees. So, using 14 as the numerator and 28 as the denominator and then multiplying result by 100, one obtains a reduction in the annualized rate of decline of 50 percent.

In general, the methods of this invention provide for an average percent reduction in functionality for a cohort of at least 30% and, more preferably, at least about 35%, or at least about 40%, or at least about 45%, or at least about 50%, or at least about 55%, or at least about 60% or more over either a 3 month, a 6 month, or annually. The rate of decline can be measured over any time period intermediate between 3 months and 1 year.

Methodology—Deuterated Arachidonic Acid

Some of the methods of this invention utilize direct administration of deuterated arachidonic acid or an ester thereof in order to bypass the biosynthesis of deuterated arachidonic acid from deuterated linoleic acid.

In one embodiment, 13,13-D2-arachidonic acid or ester thereof is administered to the patient in sufficient amounts to generate a concentration of 13,13-D2-arachidonic acid in the red blood cells of at least about 3% based on the total number of fatty acids found therein.

In one embodiment, such administration comprises the use of a dosing regimen that includes two dosing components. The first dosing component comprises a primer dose of 13,13-D2-arachidonic acid or an ester thereof. The second dosing component comprises a maintenance dosing amount of 13,13-D2-arachidonic acid or an ester thereof wherein the amount of 13,13-D2-arachidonic acid or an ester thereof in said maintenance dose is less than that of the first dosing component.

As to the primer dose, the amount of 13,13-D2-arachidonic acid or an ester thereof employed is preferably designed to provide rapid onset of therapy. Such therapy is measured by a reduction in the disease progression of ALS as described above. The first dosing component takes into account the various complicating factors such as the amount of PUFAs consumed by the patient in a given day as well as the general turnover rate of lipids in the cell membrane.

Regarding this last point, the lipid components of either red blood cells or motor neurons are not static but, rather, are exchanged over time. In general, only a fraction of the lipids in the cell are replaced each day. In the case of motor neurons, these cells are rich in lipids comprising arachidonic acid. The turnover of arachidonic acid in these membranes occurs from a stable pool of lipids comprising arachidonic acid in the spinal fluid. In turn, this stable pool is replaced and replenished over time by arachidonic acid included in the newly consumed lipids by the patient as part of the patient's diet as well as by biosynthesis of arachidonic acid from linoleic acid by the liver.

Hence, the choice of a dosing of 13,13-D2-arachidonic acid must address each of the above components and set a dosing level that allows for the accumulation of a sufficient amount of 13,13-D2-arachidonic acid in the body and, hence, the generation of a therapeutic level of 13,13-D2-arachidonic acid. This acceptable level is then incorporated into the pool of arachidonic acid found in the lipids that are available to exchange with lipids comprising arachidonic acid that are replaced over time in the motor neurons.

Given the above, the dosing regimen described herein must include sufficient amounts of 13,13-D2-arachidonic acid that are absorbed into the patient and when its concentration is stabilized in the lipid pool of the patient. Stabilization is reached, once the amount of deuterated 13,13-D2-arachidonic acid removed from the body is replaced by an equivalent amount of newly formed 13,13-D2-arachidonic acid. During this process, 13,13-D2-arachidonic acid is systemically absorbed into the cells of the body wherein the rate of which such absorption occurs is based on the exchange rate or turnover rate of lipids in the cell membrane of these motor neurons.

This invention is based on the discovery that given the above variables, the amount of 13,13-D2-arachidonic acid or ester thereof that is administered over time is such that the concentration of 13,13-D2-arachidonic acid in red blood cells comprises at least about 3% and preferably at least 5% of the total fatty acids found therein. At that level, the deuterated arachidonic acid concentration reduces the rate of disease progression and limits or prevents the cascade of lipid auto-oxidation. When so administered, there is a significant reduction in the progression rate of ALS.

Alternatively, the deuterated arachidonic acid or ester thereof that is administered to the patient is either a D4-arachidonic acid or ester (as described above) or a 7,7,10,10,13,13-D6-arachidonic acid or an ester thereof. Because either two or three of the bis-allylic carbon atoms on these compounds have the hydrogens replaced with deuterium, these compounds will provide superior reduction in the reducing or eliminating lipid auto-oxidation. As such, less of these compounds will be required to provide a meaningful reduction in the rate of progression of ALS. In a preferred embodiment, these D4- or D-6arachidonic acids or esters thereof are delivered in a tiered manner comprising a first and second dosing component. The first dosing component, the primer dose, follows the protocol set forth above with the exception that the primer uses between about 0.5 and about 5 grams of 7,7,10,10,13,13-D6-arachidonic acid or an ester thereof daily or periodically whereas the D4-arachidonic acids or esters use between about 1 ant 6 grams as the primer dose. In both cases, the maintenance dose, uses between 30% and 70% of the primer dose.

The reduction in the rate of disease progression is evaluated as set forth above and provides for the same degree of reduction as also described above.

Other deuterated arachidonic acid or ester compounds will typically correspond to the above dosing regimen understanding that the degree of protection may increase or decrease depending on the extent of deuteration.

Combinations

The therapy provided herein can be combined with conventional treatment of ALS provided that such therapy is operating on an orthogonal mechanism of action relative to inhibition of lipid auto-oxidation. Suitable drugs for use in combination include, but not limited to, anti-oxidants such as edaravone, idebenone, mitoquinone, mitoquinol, vitamin C, or vitamin E that are not directed to inhibiting lipid auto-oxidation, riluzole which preferentially blocks TTX-sensitive sodium channels, conventional pain relief mediations, and the like.

Pharmaceutical Compositions

The specific dosing of a deuterated linoleic acid or an ester thereof or a deuterated arachidonic acid ("drug") administered to a patient can be accomplished by any number of the accepted modes of administration. As noted above, the actual amount of the drug used in a daily or periodic dose per the methods of this invention, i.e., the active ingredient, is described in detail above. The drug can be administered at least once a day, preferably once or twice or three times a day.

This invention is not limited to any particular composition or pharmaceutical carrier, as such may vary. In general, compounds of this invention will be administered as pharmaceutical compositions by any of a number of known routes of administration. However, orally delivery is preferred typically using tablets, pills, capsules, and the like.

The particular form used for oral delivery is not critical but due to the large amount of drug to be administered, a daily or periodic unit dose is preferably divided into subunits having a number of tablets, pills, capsules, and the like. In one particularly preferred embodiment, each subunit of the daily or periodic unit dose contains about 1 gram of the drug. So, a daily or periodic unit dose of 9 grams of the drug is preferably provided as 9 sub-unit doses containing about 1 gram of the drug. Preferably, the unit dose is taken in one setting but, if patient compliance is enhanced by taking the daily or periodic unit dose over 2 or 3 settings per day, such is also acceptable.

Pharmaceutical dosage forms of a compound of this invention may be manufactured by any of the methods well-known in the art, such as, by conventional mixing, tableting, encapsulating, and the like. The compositions of this invention can include one or more physiologically acceptable inactive ingredients that facilitate processing of active molecules into preparations for pharmaceutical use.

The compositions can comprise the drug in combination with at least one pharmaceutically acceptable excipient. Acceptable excipients are non-toxic, aid administration, and do not adversely affect the therapeutic benefit of the claimed compounds. Such excipient may be any solid, liquid, or semi-solid that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Other suitable pharmaceutical excipients and their formulations are described in *Remington's Pharmaceutical Sciences*, edited by E. W. Martin (Mack Publishing Company, 18th ed., 1990).

The compositions of this invention may, if desired, be presented in a pack or dispenser device each containing a daily or periodic unit dosage containing the drug in the required number of subunits. Such a pack or device may, for example, comprise metal or plastic foil, such as a blister pack, a vial, or any other type of containment. The pack or dispenser device may be accompanied by instructions for administration including, for example, instructions to take all of the subunits constituting the daily or periodic dose contained therein.

The amount of the drug in a formulation can vary depending on the number of subunits required for the daily or periodic dose of the drug. Typically, the formulation will contain, on a weight percent (wt %) basis, from about 10 to 99 weight percent of the drug based on the total formulation, with the balance being one or more suitable pharmaceutical excipients. Preferably, the compound is present at a level of about 50 to 99 weight percent.

EXAMPLES

This invention is further understood by reference to the following examples, which are intended to be purely exemplary of this invention. This invention is not limited in scope by the exemplified embodiments, which are intended as illustrations of single aspects of this invention only. Any methods that are functionally equivalent are within the scope of this invention. Various modifications of this invention in addition to those described herein will become apparent to those skilled in the art from the foregoing description and accompanying figures. Such modifications fall within the scope of the appended claims. In these examples, the following terms are used herein and have the following meanings. If not defined, the abbreviation has its conventional medical meaning.

D2-AA=13,13-D2-Arachidonic Acid
AA=Arachidonic Acid
ALSFRS-R=Revised ALS Functional Rating Scale
CNS=Central Nervous System
D2-LA=11,11-D2-Linoleic Acid
LA=Linoleic Acid
PK=Pharmacokinetics
RBC=Red Blood Cells
SAE=Serious Adverse Events
SF=Spinal Fluid
% deuterated PUFA=Percentage of the phospholipid containing a deuterated PUFA is based on the total amount of the phospholipid in the cell being analyzed Example 1—AA Concentrations in RBCs and Spinal Fluid This example was designed to evaluate how to calculate the concentration of D2-AA in the SF based on its concentration or the concentration of D2-linoleic acid in RBCs. Specifically, two separate correlations were done allowing for the calculation of either D2-LA or D2-AA in RBCs to provide a corresponding concentration of D2-AA in spinal fluid and, accordingly, in the motor neurons of the CNS. This proxy concentration allows the clinician a relatively facile means to measure the concentration of D2-AA in the spinal fluid without having to obtain spinal fluid from the patient.

In this example, a patient was continuously provided a daily dose of 9 grams of D2-LA ethyl ester over about a three-month period. Periodic samples of blood and SF were taken and the concentration of both D2-LA and D-2AA in both the RBCs and the SF were measured. In all cases, the D2-AA was obtained by deacylation of the ethyl ester followed by hepatic conversion of D2-LA in vivo. Table 2 shows that the ratio of D2-LA:D2-AA in the SF at one month was about 2.5:1.

TABLE 2

| Time | Concentration of D2-LA in SF | Concentration of D2-AA in SF | Ratio of D2-LA to D2-AA in SF |
|---|---|---|---|
| 1 month | 19.8% | 8% | 2.5:1 |

Next, Table 3 shows that the concentration of D2-LA and D2-AA in the RBCs at 3 months and at 6 months. Here the ratio of D2-LA to D2-AA at 3 and 6 months is 2.5:1+/−0.4.

TABLE 3

| Time | Concentration of D2-LA in RBCs | Concentration of D2-AA in RBCs | Ratio of D2-LA to D2-AA in RBCs |
|---|---|---|---|
| 3 months | 34.7% | 11.8% | 2.9:1 |
| 6 months | 34.5% | 16.7% | 2.1:1 |

So, one can correlate that the concentration of D2-AA is about 2 5 times less than the concentration of D2-LA whether in RBCs or SF.

Example 2—Stabilization of the Rate of Disease Progression

This example illustrates the reduction in the rate of disease progression in patients with ALS treated by the dosing methods of this invention. Specifically, a cohort of 3 patients was placed on a dosing regimen consisting of a first dosing component (primer dose) of about 9 grams of D2-LA ethyl ester daily for a period of at least 30 days and then all three patients were transitioned to a second dosing component (maintenance dose) of 5 grams of D2-LA ethyl ester.

The functionality of each of the patients was evaluated periodically using the ALSFRS-R protocol. The patients continued on the dosing regimen for a period of 6 months (patient A) or 1 year (patient B) or for 9 months (patient C). Patient C died at the end of 9 months and his death was attributed to factors other than ALS cardiomyopathy. Before initiation of therapy, the natural history of each patient in the cohort was determined and an average annual rate of functional decline was measured at 21.

The annualized progression of the disease as measured by an average annual rate of functional decline for all three patients starting at the time that dosing began and terminating at the end of the dosing regimen and then annualized as described above was measured as 2.1. Using the formula described above, one obtains the following:

$(21-2.1)/21 \times 100 = 90\%$ annualized average reduction in the rate of disease progression.

The specific values for each of the three members of the cohort are as follows in Table 5:

TABLE 5

| Patient | NH Rate of Decline | Functional Rate Decline During Therapy |
|---|---|---|
| A | −16 | −3 |
| B | −31 | −2 |
| C | −16 | −1.3 |

NH = Natural History

These results substantiate a very significant rate of reduction and stabilization in the disease progression using the dosing regimen as per this invention. These results also substantiate that transitioning patients from a primer dose to a maintenance dose maintains the beneficial stabilization in the rate of decline.

Even when the rate of decline for patient B is removed, the average rate of decline for the two remaining patients' natural history is −16 whereas the average rate of decline during the treatment period is 2.15. This provides for an 84% average rate of reduction in the disease progression. In addition, this example demonstrates that the tiered dosing protocol provides for exceptional reduction in the rate of disease progression.

The invention claimed is:

1. A method for reducing disease progression of ALS in a patient, the method comprising:
    administering 11,11-D2-linoleic acid or an ester thereof to the patient with a dosing regimen that comprises a primer dose and a maintenance dose thereby reducing said disease progression in said patient;
    a) said primer dose comprises about 9 grams of 11,11-D2-linoleic acid or an ester thereof per day wherein said primer dose is continued for about 30 days to 45 days to rapidly achieve a therapeutic concentration of 13,13-D2-arachidonic acid in vivo due to hepatic conversion of a portion of said 11,11-D2-arachidonic acid to 13,13-D2-arachidonic acid thereby reducing the rate of disease progression; and b) subsequent to the about 30 days to 45 days of administering said primer dose, administering said maintenance dose of about 5 grams of 11,11-D2-linoleic acid or an ester per day thereof to maintain said therapeutic concentration of 13,13-D2-arachidonic acid in vivo such that the rate of disease progression is reduced provided that said reduction is measured to be at least about 30% reduction relative to the rate of disease progression during the natural history of the patient.

2. The method of claim 1, wherein a percent reduction in the rate of disease progression is determined by:

measuring a natural rate of disease progression in a patient or an average natural rate of disease progression in a cohort of patients;

measuring the rate of disease progression in said patient or cohort of patients during a period of compliance with the administering step; and calculating the difference between the natural rate and the rate during the period of compliance, dividing the difference by the rate of disease progression during the natural history of the patient, and multiplying by 100.

3. The method of claim 1, which further comprises restricting the patient's consumption of excessive dietary polyunsaturated fatty acids during administration of said primer and said maintenance doses.

4. The method of claim 1, wherein said primer dose and/or said maintenance dose is provided in 1, 2 or 3 sittings.

* * * * *